(12) United States Patent
Armitage et al.

(10) Patent No.: US 8,431,732 B2
(45) Date of Patent: Apr. 30, 2013

(54) CARBONYLATION PROCESS FOR THE PRODUCTION OF METHYL ACETATE

(75) Inventors: Gareth Gerald Armitage, York (GB); Evert Jan Ditzel, North Humberside (GB); David John Law, Beverley (GB); John Glenn Sunley, Cottingham (GB)

(73) Assignee: BP Chemicals Limited, Middlesex (GB)

( * ) Notice: Subject to any disclaimer, the term of this patent is extended or adjusted under 35 U.S.C. 154(b) by 230 days.

(21) Appl. No.: 12/735,121

(22) PCT Filed: Dec. 16, 2008

(86) PCT No.: PCT/GB2008/004142
§ 371 (c)(1),
(2), (4) Date: Jun. 17, 2010

(87) PCT Pub. No.: WO2009/077743

PCT Pub. Date: Jun. 25, 2009

(65) Prior Publication Data

US 2010/0274045 A1    Oct. 28, 2010

(30) Foreign Application Priority Data

Dec. 19, 2007 (EP) .................................... 07254956

(51) Int. Cl.
*C07C 67/36* (2006.01)
(52) U.S. Cl.
USPC ..................................................... 560/232
(58) Field of Classification Search .......... None
See application file for complete search history.

(56) References Cited

U.S. PATENT DOCUMENTS 7,465,822 B2 * 12/2008 Cheung et al. ............... 560/232
2006/0252959 A1 * 11/2006 Cheung et al. ............... 560/232

FOREIGN PATENT DOCUMENTS

| EP | 0 596 632 | 5/1994 |
| EP | 0596632 | * 5/1994 |
| JP | 11-147042 | 6/1999 |
| WO | 2007/128955 | 11/2007 |
| WO | 2007128955 | * 11/2007 |

OTHER PUBLICATIONS

International Search Report for PCT/GB2008/004142, mailed May 11, 2009.
Written Opinion of the International Searching Authority for PCT/GB2008/004142, mailed May 11, 2009.
International Preliminary Report on Patentability for PCT/GB2008/004142, mailed Mar. 25, 2010.
Fujimoto et al., "Vapor Phase Carbonylation of Methanol with Solid Acid Catalysts", Chemistry Letters, Chemical Society of Japan, Tokyo, 1984, pp. 2047-2050, XP002484459.
Cheung et al., "Selective Carbonylation of Dimethyl Ether to Methyl Acetate Catalyzed by Acidic Zeolites", Angewandte Chemie. International Edition, vol. 45, No. 10, Jan. 1, 2006, pp. 1617-1620, XP002453571.

(Continued)

*Primary Examiner* — Karl J Puttlitz
(74) *Attorney, Agent, or Firm* — Nixon & Vanderhye (57) ABSTRACT

Process for the manufacture of methyl acetate by carbonylating a carbonylatable reactant selected from dimethyl ether and dimethyl carbonate containing less than 2.5 wt % water with carbon monoxide in the presence of a mordenite catalyst. The mordenite has been ion-exchanged with at least one Group IB metal, and the molar ratio of the Group IB metal to total aluminum present in the mordenite is in the range 5 to 50 mol %.

15 Claims, 5 Drawing Sheets

OTHER PUBLICATIONS

Ellis et al., "Heterogeneous Catalysts for the Direct, Halide-free Carbonylation of Methanol", Studies in Surface Science and Catalysis, Elsevier Science B.V., Amsterdam, vol. 101, 1996, pp. 771-779, XP009101682.

* cited by examiner

CARBONYLATION PROCESS FOR THE PRODUCTION OF METHYL ACETATE

This application is the U.S. national phase of International Application No. PCT/GB2008/004142, filed 16 Dec. 2008, which designated the U.S. and claims priority to European Application No. 07254956.1, filed 19 Dec. 2007, the entire contents of each of which are hereby incorporated by reference.

This invention relates to a carbonylation process for the production of methyl acetate from dimethyl ether and/or dimethyl carbonate in the presence of a Group IB metal loaded mordenite zeolite catalyst, and, in particular to a Group IB metal loaded mordenite zeolite catalyst which has been prepared by ion-exchange.

BACKGROUND OF THE INVENTION

Mordenite which has been loaded with metals such as copper and silver are known to be suitable for use as catalysts for the carbonylation of feedstocks such as methanol, dimethyl ether and dimethyl carbonate to produce the carbonylation products methyl acetate and/or acetic acid.

EP-A-0 596 632 describes a vapour phase process for the carbonylation of methanol to produce acetic acid in the presence of a mordenite loaded with copper, nickel, iridium, rhodium or cobalt catalyst at high temperatures and pressures. The preparation of copper, rhodium and iridium loaded mordenites by wet impregnation of the metal salt solutions is described.

WO 2005/105720 describes a process for production of a carboxylic acid and/or an ester or anhydride thereof by carbonylating an aliphatic alcohol or reactive derivative thereof with carbon monoxide in the substantial absence of halogens in the presence of mordenite loaded with copper, nickel, iridium, rhodium or cobalt and having as framework elements, silicon, aluminium and at least one of gallium, boron and iron at a temperature in the range 250-600° C. and a pressure in the range 10 to 200 bar.

WO 2006/121778 describes a process for the production of a lower alkyl ester of a lower aliphatic carboxylic acid by carbonylating under substantially anhydrous conditions a lower alkyl ether with carbon monoxide in the presence of a mordenite or ferrierite catalyst optionally loaded with copper, nickel, iridium, rhodium, platinum, palladium or cobalt. The preparation of a metal loaded mordenite or ferrierite is not described in WO 2006/121778.

'Carbonylation of methanol on metal-acid zeolites: Evidence for a mechanism involving a multisite active center' by T Blasco et al, Angew. Chem. Int Ed. 2007, 46, 3938-3941 describes the ion-exchange of H-mordenite with copper. The amount of copper in the resultant mordenite is stated to be 2.5 wt %.

Metal loaded catalysts are generally expensive to prepare due to the cost of the metal. Thus, there is a need for catalysts which contain a reduced amount of metal but which retain comparable catalytic performance to those containing higher amounts of the same metal.

SUMMARY OF THE INVENTION

It has now been found that, in the carbonylation of dimethyl ether and/or dimethyl carbonate, the use of a Group IB metal loaded mordenite catalyst in which the Group IB metal has been loaded onto the mordenite by ion-exchange, enables improved activities and/or selectivities to be achieved compared to a mordenite catalyst having the same amount of Group IB metal but which catalyst has been prepared by a different technique. Conversely, the use of Group IB metal loaded mordenites prepared by ion-exchange allows improved or comparable activities and/or selectivities to be achieved in carbonylation processes, but at much lower metal loadings than in Group IB metal loaded mordenites prepared by alternative methods.

Accordingly, the present invention provides a process for the manufacture of methyl acetate by the carbonylation of a carbonylatable reactant selected from dimethyl ether and dimethyl carbonate with carbon monoxide under substantially anhydrous conditions in the presence of a mordenite catalyst, wherein said mordenite has been ion-exchanged with at least one Group IB metal and the molar ratio of the Group IB metal to total aluminium present in the mordenite is in the range 5 to 50 mol %.

The structure of mordenite is well-known and defined, for example, in the Atlas of Zeolite Framework Types (C. Baerlocher, W. M. Meier, D. H. Olson, $5^{th}$ ed. Elsevier, Amsterdam, 2001) and the web-based version thereof (http://www.iza-structure.org/databases/) which is a compendium of topological and structural details about zeolite frameworks.

Mordenite is available from commercial sources, generally in the Na, $NH_4$ form or H-form of the mordenite. The $NH_4$ form can be converted to the acid (H-form) by known techniques, such as calcination at high temperature. The Na form can be converted to the acid (H-form) by converting first to an $NH_4$ form by ion exchange with ammonium salts such as ammonium nitrate.

Typically, mordenite has a silica:alumina ratio in the range 8:1 to 50:1. For use in the carbonylation process of the present invention, the mordenite preferably has a silica:alumina ratio in the range 15:1 to 40:1.

Before use as a catalyst in the carbonylation process, the mordenite is loaded with a metal selected from at least one Group IB metal. Group IB metals are copper, silver and gold.

The Group IB metal loaded mordenite is prepared by the ion-exchange of the cation-exchangeable sites of the mordenite with at least one Group IB metal. The following ion-exchange method may be employed to prepare a Group IB metal loaded mordenite. Mordenite in a suitable form, such as H-mordenite or $NH_4$-mordenite, is contacted with an aqueous solution of a metal salt selected from a copper (I) or (II) salt, a silver (I) salt or a gold (I) salt.

Suitable copper (I) salts include copper halides, such as copper chloride, and copper acetate.

Suitable copper (II) salts include copper nitrate, copper acetate, copper sulphate, copper oxalates, copper halides such as copper chloride.

Suitable silver (I) salts include silver nitrate, silver acetate, silver triflate.

In the presence of white light silver salts tend to undergo light promoted reduction to silver metal so it is preferred that the ion-exchange is carried out in the substantial absence of light.

Suitable gold (I) salts include gold chloride and gold nitrate.

Mixtures of copper, silver and gold salts may be used, such as a mixture of copper and silver salts.

The metal salts are used in the form of an aqueous solution by dissolving the salts in any suitable solvent. Suitable solvents include deionised water and a solution of ammonium hydroxide in deionised water.

Where the mordenite is to be ion-exchanged with more than one metal, the metals may be loaded sequentially or simultaneously. For example, where the mordenite is to be loaded with copper and silver, the mordenite may be contacted with a single aqueous solution of copper and silver salts. Alternatively, the mordenite may be first contacted with a solution of a silver salt and then a solution of a copper salt.

The amount of each metal salt used is such that the exchanged mordenite has a metal loading within the range 5 to 50 mol % relative to the total aluminium in the mordenite.

The mordenite is contacted with the metal salt solution such that the mordenite is at or above its level of incipient wetness.

Optionally, to improve the rate of metal exchange, the mordenite/aqueous solution mixture may be heated provided that the level of incipient wetness is maintained and the residual metal salt solution remains as a solution. At atmospheric pressure, a suitable temperature may be in the range 60 to 90° C. The solution may be heated until the desired level of metal loading is reached.

The optionally heated solution is then filtered to remove excess metal salt solution and to recover a solid metal loaded mordenite. The filtering may be carried out using conventional filtration techniques such as vacuum filtration.

After filtering, the solid metal loaded mordenite is washed with a solvent in which the metal salt solution is soluble and which solvent does not remove the exchanged metal from the mordenite. Suitable solvents include deionised water.

Preferably, the washed metal loaded mordenite is then dried to remove residual water to achieve a free-flowing powder. Preferably, drying is carried out by heating the metal loaded mordenite to a temperature of at least 90° C., for example 90 to 120° C. The heating may be conducted in static or free-flowing air or in an inert gas such as nitrogen.

Prior to use in the carbonylation process, the metal loaded mordenite may be calcined at a temperature in the range 400 to 600° C. The calcination may be carried out in static or free-flowing air or in an inert gas such as nitrogen.

The method of the present invention enables mordenite catalysts to be prepared which have reduced metal loadings compared to mordenite catalysts produced by other preparation methods such as total evaporation impregnation or incipient wetness.

Advantageously, these reduced metal mordenites may exhibit improved catalyst activity over equivalent catalysts prepared by other preparation techniques, such as total evaporation impregnation. Thus, the method of the present invention enables an improved catalyst to be produced at lower cost. Furthermore, due to the lower quantities of metals present in the mordenites of the present invention, the mordenite catalyst will have a reduced tendency to deactivate through the deactivation mechanisms of sintering and agglomeration of metal particles present in the mordenite, thereby enhancing the life of the mordenite catalyst.

The Group IB metal loading on a mordenite may be expressed in terms of the fractional loading of the metal as gram atoms of metal per gram atom of aluminium in the mordenite. The metal loading can also be expressed as a mole percentage loading relative to the total aluminium in the mordenite through the relationship:

mol % Metal=(gram atoms Metal/gram atoms aluminium)×100

By total aluminium is meant the total aluminium in the bulk mordenite. The bulk mordenite includes the framework aluminium and, if any, extra-framework aluminium.

Thus, for example, a loading of 0.55 gram atoms of copper per aluminium in the mordenite equates to a 55 mol % loading of copper relative to the total aluminium in the mordenite.

The Group IB metal loading may be in the range of 5 to 50 mol % relative to aluminium, for example, 10 to 45 mol %.

Preferably, where the Group IB metal is copper, the copper loading is in the range 5 to 30 mol %, such as 10 to 20 mol % relative to the total aluminium in the mordenite.

Preferably, where the Group IB metal is silver, the silver loading is in the range 5 to 40 mol % relative to the total aluminium in the mordenite.

Where the mordenite is to be loaded with more than one Group IB metal, such as a mixture of silver and copper, the total metal loading is 5 to 50 mol % relative to the total aluminium in the mordenite.

The carbonylation process is typically carried out by passing the dimethyl ether and/or dimethyl carbonate and carbon monoxide through a fixed or fluidised bed of the Group IB metal loaded mordenite catalyst maintained at the required temperature, such as in the range 150 to 350° C., such as 250 to 350° C.

The carbonylation process is carried out under substantially anhydrous conditions, that is less than 2.5 wt % water in the dimethyl ether or dimethyl carbonate feed.

The carbonylation process may be carried out at a total reaction pressure in the range 1 to 100 bar.

The carbonylation process may be carried out at a gas hourly space velocity (GHSV) of the carbonylatable reactant feed in the range 500 to 40,0000 $h^{-1}$.

It is preferred that the catalyst is dried prior to use. The catalyst may be dried, for example by heating to a temperature of 400 to 500° C.

Suitably, the catalyst is activated, immediately before use in the carbonylation reaction, by heating the catalyst at elevated temperature for at least one hour under flowing nitrogen, carbon monoxide, hydrogen or mixtures thereof.

The carbon monoxide employed in the carbonylation process may be substantially pure carbon monoxide, for example, carbon monoxide typically provided by suppliers of industrial gases, or it may contain impurities that do not interfere with the conversion of the methanol to acetic acid or the conversion of dimethyl ether or dimethyl carbonate to methyl acetate, such as nitrogen, helium, argon, methane and/or carbon dioxide.

The carbonylation process may be conducted in the presence of hydrogen, thus the carbon monoxide feed may contain hydrogen. Mixtures of hydrogen and carbon monoxide are commercially produced by the steam reforming of hydrocarbons and by the partial oxidation of hydrocarbons. Such mixtures are commonly referred to as synthesis gas. Synthesis gas comprises mainly carbon monoxide and hydrogen but may also contain smaller quantities of carbon dioxide. The molar ratio of carbon monoxide:hydrogen may be in the range 1:3 to 15:1. The molar ratio of carbon monoxide to methanol or dimethyl ether or dimethyl carbonate may be in the range 1:1 to 99:1.

The primary product of the carbonylation process is methyl acetate but small amounts of acetic acid may also be produced. The methyl acetate product can be removed in the form of a vapour and thereafter condensed to a liquid.

The methyl acetate may be recovered and sold as such or it may be forwarded to other chemical processes. Where the methyl acetate is recovered from the carbonylation reaction products, some or all of it may be hydrolysed to form acetic acid. Alternatively, the entire carbonylation reaction product may be passed to a hydrolysis stage and acetic acid separated thereafter. The hydrolysis may be carried out by known techniques such as reactive distillation in the presence of an acid catalyst.

The carbonylation process may be run as a continuous or a batch process, preferably a continuous process.

BRIEF DESCRIPTION OF THE DRAWINGS

The invention is further described with reference to the accompanying drawings, in which.

The invention is now illustrated with reference to the following Examples.

Preparation of Ag-Mordenite by Ion-Exchange (Catalyst A)

NH$_4$-mordenite (10 g) with a silica to alumina ratio of 20 (CBV21A ex Zeolyst) was added to a 100 ml autoclave bomb containing an aqueous solution of silver(I) nitrate (1.36 g) in deionised water (100 ml) and placed in an autoclave oven set at 100° C. and stirred with rapid rotation for 3 hours. After this time the autoclave bomb was removed from the oven and the solution/suspension was filtered through a sinter funnel and the collected solid mordenite was washed with copious amounts of deionised water. After washing the mordenite was transferred to a drying oven set at 90° C. for 2 hours, before being calcined at 500° C. for 3 hours. The mordenite (ca. 0.75 g at a time) was then compacted at 10 tonnes in a 13 mm die set using a pneumatic press, and crushed and sieved to a particle size fraction of 125 to 160 microns. ICP spectroscopic analysis showed the mordenite to contain 5.2 wt % Ag and 3.3 wt % Al equating to a silver loading of 39 mole % relative to aluminium.

Preparation of Cu-Mordenite by Ion Exchange (Catalyst B)

NH4-mordenite (10 g) with a silica to alumina ratio of 20 (ex Zeolyst) was treated with an aqueous solution of copper (II) nitrate hydrate (0.742 g) in deionised water (100 mL) and stirred at 80° C. for 2 hours. The solution/suspension was then filtered through a sinter funnel and the collected solid was washed with copious amounts of deionised water. After washing the mordenite was dried, calcined, compacted, crushed and sieved in accordance with the procedures described in the preparation of Catalyst A. ICP spectroscopic analysis showed the mordenite to contain 1.3 wt % Cu and 3.8 wt % Al. equating to a copper loading of 15 mole % relative to aluminium.

Preparation of Ag-Mordenite by Impregnation (Catalyst D)

NH$_4$-mordenite (25.05 g) with a silica to alumina ratio of 20 (ex Zeolyst) was weighed into a 250 mL round bottomed flask with a stirrer bar 3.2726 g of silver (I) nitrate was dissolved in a minimum amount of deionised water. This solution was added to the mordenite along with sufficient deionised water (ca. 150 mL) to give a mobile slurry. The top of the flask was then covered loosely and the flask left to stir overnight. The mordenite was then dried under reduced vacuum using a rotary evaporator before being dried in an oven at 90° C. for 1-2 hours. The dried mordenite was calcined in a muffle oven (oven volume=18 L) under a static atmosphere of air by heating at 90° C. for 2 hours, heating at 110° C. for 2 hours and then heating at 500° C. for 3 hours. The calcined mordenite was compacted, crushed and sieved in accordance with the procedure described in the preparation of Catalyst A. ICP spectroscopic analysis showed the mordenite to contain 8.2 wt % Ag and 3.6 wt % Al, equating to a silver loading of 57 mole % relative to aluminium.

Preparation of Cu-Mordenite by Impregnation (Catalyst E)

Preparation D was repeated except that 24.96 g of NH$_4$-mordenite was employed and 4.6349 g of copper (II) nitrate hydrate dissolved in a minimum amount of deionised water was used in place of the silver nitrate. ICP spectroscopic analysis showed the mordenite to contain 5.3 wt % Cu and 3.8 wt % Al, equating to a copper loading of 59 mole % relative to aluminium.

EXAMPLES 1 to 5

Carbonylation of Dimethyl Ether Using Catalysts A, B, D and E

Each of the mordenite catalysts A, B, D and E were used to catalyse the carbonylation of dimethyl ether (DME) with carbon monoxide. The experiments were carried out in a pressure flow reactor unit consisting of 16 identical reactors of the type described in WO 2005063372. Prior to loading of a catalyst into a reactor, a ca. 5 cm bed of steatite of sieve fraction of 100-350 μm was placed in the respective catalyst holder. A ca. 5 cm zone of corundum of sieve fraction of 125-160 μm was placed on top of the steatite bed. On a dry mass basis (determined by loss on ignition of the relevant catalyst measured by heating the catalyst from room temperature to 600° C. at a ramp rate of ca. 30° C. per minute). 0.625 g (ca. 1 ml) of a catalyst was then placed on top of the corundum bed. The catalyst was covered by a ca. 5 cm corundum bed of a particle size of 125-160 μm. A ca. 5 cm zone of steatite of sieve fraction of 100-350 μm was placed on top of the corundum bed. Every zone was concreted via hitting or vibrating to get a stable bed and a defined starting height of the catalyst zone. The catalyst was then pressurised to the desired reaction pressure of 70 bar. Carbon monoxide and hydrogen in a 4:1 molar ratio was introduced into the reactor at a flow rate of 4 l/h. The catalyst was then heated at 0.5° C./min to a holding temperature of 220° C., where it was held for a dwell time of 3 hours. Subsequently the temperature was ramped to 300° C. at 0.5° C./min, followed by a further dwell time of 3 hours. The gas feed was Then changed to a mixture of carbon monoxide, hydrogen and dimethyl ether at a molar ratio of 72/18/10 and a flow rate of 4 l/h, with the dimethyl ether fed as a vapour at 0.4 l/h to obtain a CO/H$_2$/DME molar ratio in the total feed of 72/18/10. Nitrogen gas was introduced at a variable rate of 0-50 ml/min to equalise the pressure swings between the 16 reactor exits. The exit stream from the each reactor was passed to a gas chromatograph to determine the concentration of reactants and carbonylation products. The reaction was allowed to continue for 97 hours under conditions of 300° C., 70 bar total pressure, a gas GHSV of 4000 h$^{-1}$ and a CO/H$_2$/DME molar ratio in the total feed of 72/18/10. The results of the carbonylation reactions are given in FIGS. 1 to 3.

Figure 1:
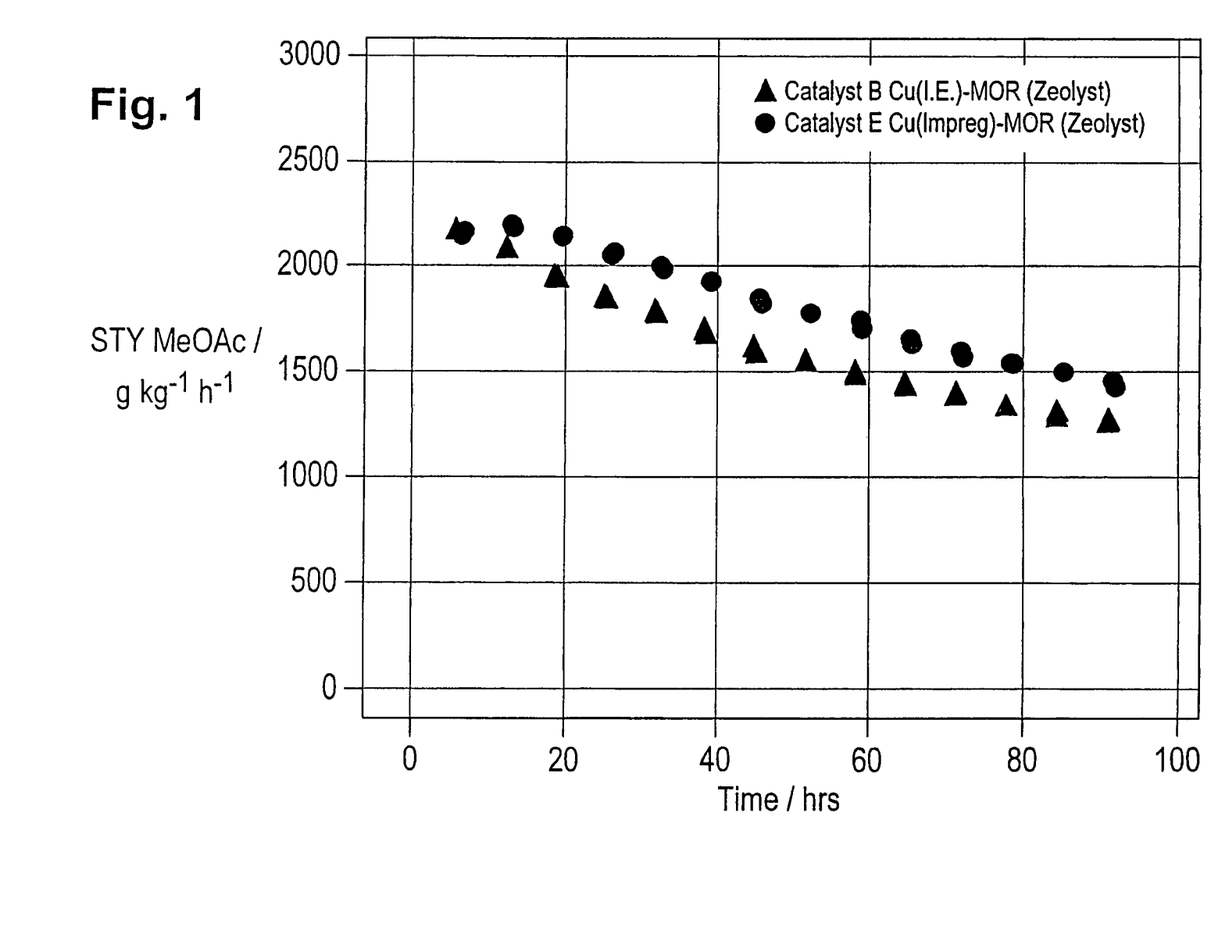
FIG. 1 depicts the STY to methyl acetate product in g kg$^{-1}$ h$^{-1}$ versus time. on stream for Cu-mordenite catalysts prepared by ion exchange and impregnation techniques.

FIG. 1 shows that catalyst B prepared by ion-exchange has a similar activity to catalyst E prepared by impregnation but at a significantly lower Cu loading, 1.3 weight % Cu compared to 5.3 weight % Cu.

Figure 2:
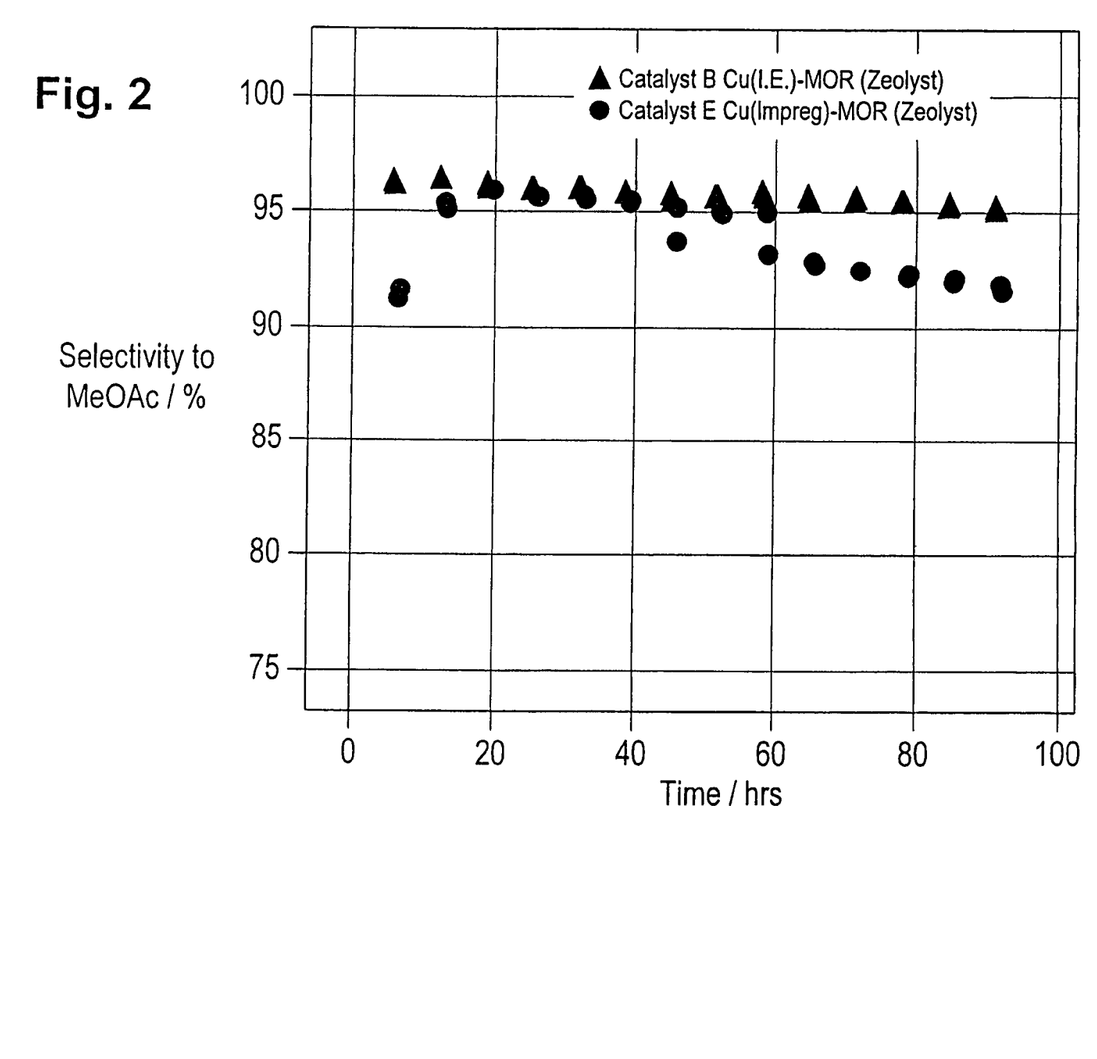
FIG. 2 depicts Selectivity to methyl acetate product versus time on stream for Cu-mordenite catalysts prepared by ion exchange and impregnation techniques.

FIG. 2 shows that catalyst B prepared by ion-exchange has in general a higher selectivity to methyl acetate (based upon dimethyl ether converted) than catalyst E prepared by impregnation.

Figure 3:
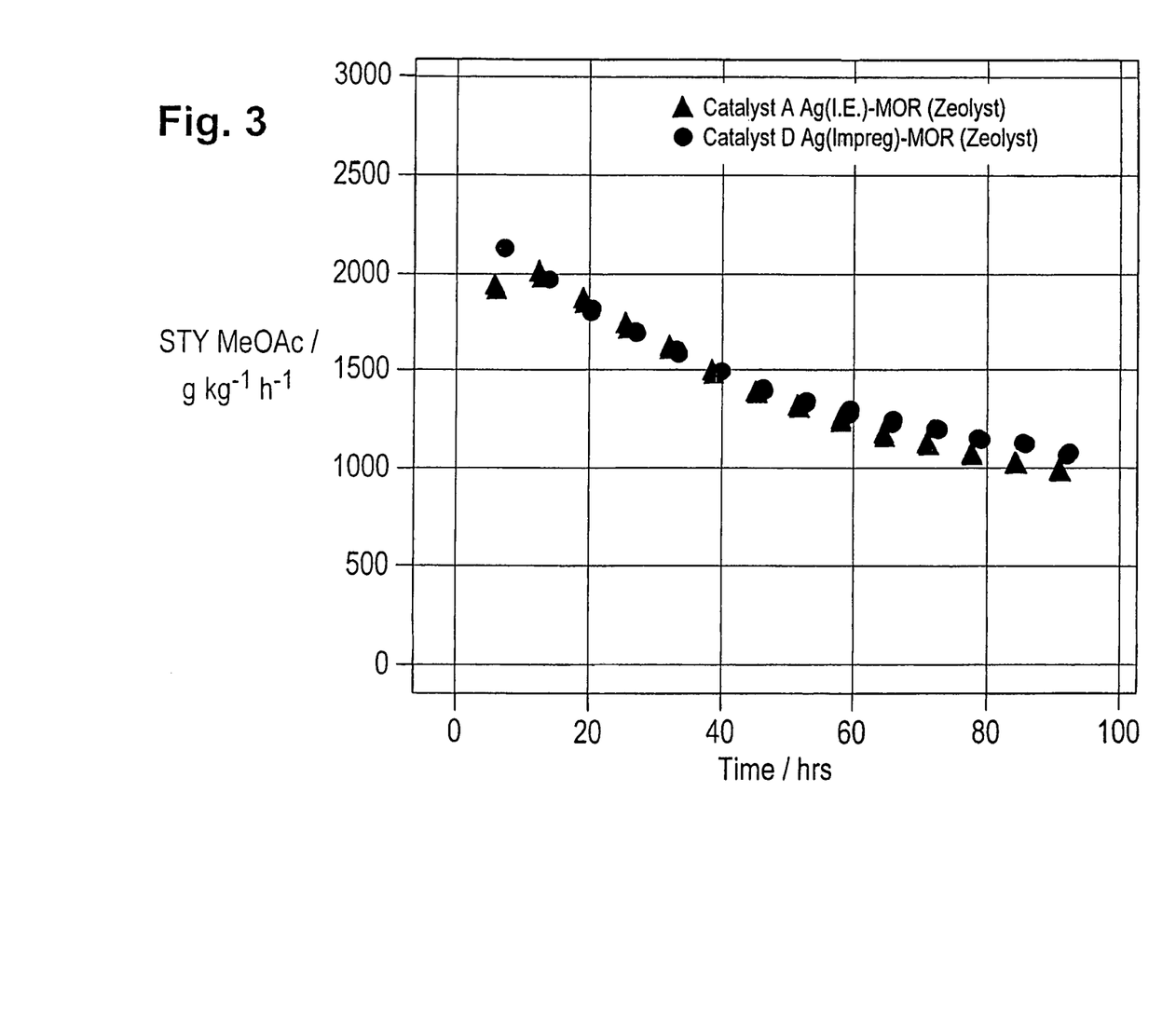
FIG. 3 depicts the STY to methyl acetate product in g kg$^{-1}$ h$^{-1}$ versus time on stream for Ag-mordenite prepared by ion exchange and impregnation techniques.

FIG. 3 shows that catalyst A prepared by ion-exchange has essentially the same activity as catalyst D prepared by impregnation but at a significantly lower Ag loading, 5.2 weight % Ag compared to 8.2 weight % Ag.

Preparation of Cu-Mordenite by Ion Exchange (Catalyst F)

Preparation of Catalyst B was repeated except that $Cu(NO_3)_2 \cdot 2.5H_2O$ (0.713 g) was used instead of copper(II) nitrate hydrate. ICP spectroscopic analysis showed the mordenite to contain 1.2 wt % Cu and 3.6 wt % Al, equating to a copper loading of 14 mole % relative to aluminium.

Preparation of Cu-Mordenite by Impregnation (Catalyst G)

$NH_4$-mordenite (10.00 g) with a silica to alumina ratio of 20 (ex Zeolyst) was weighed into a round bottomed flask with a stirrer bar 0.440 g of $Cu(NO_3)_2 \cdot 2.5H_2O$ was dissolved in 15 ml of deionised water. This solution was added to the mordenite to give a mobile slurry. The top of the flask was then covered loosely and the flask left to stir overnight. The mordenite was then dried under reduced vacuum using a rotary evaporator. The mordenite was then calcined in a muffle oven (oven volume=18 L) under a static atmosphere of air by heating at 110° C. for 20 hours and then at 500° C. for 3 hours. The calcined mordenite was compacted, crushed and sieved in accordance with the procedures described in the preparation of Catalyst A. The mordenite contained 1.2 wt % copper.

EXAMPLES 6 to 7

Carbonylation of Dimethyl Ether Using Catalysts F and G

Each of the mordenite catalyst samples F and G was used to catalyse the carbonylation of dimethyl ether with carbon monoxide using the same experimental method as for Examples 1 to 5, except that the $CO/H_2/DME$ feed was fed at a flow rate of 4.275 l/h, with the DME fed as a vapour at 0.4275 l/h, to obtain a $CO/H_2/DME$ molar ratio in the total feed of 72/18/10. The reaction was allowed to continue for 96 hours under conditions of 300° C., 70 bar total pressure, a gas GHSV of 4275 $h^{-1}$ and with a $CO/H_2/DME$ molar ratio in the total feed of 72/18/10. The results of the carbonylation reactions are given in FIGS. 4 to 5.

Figure 4:
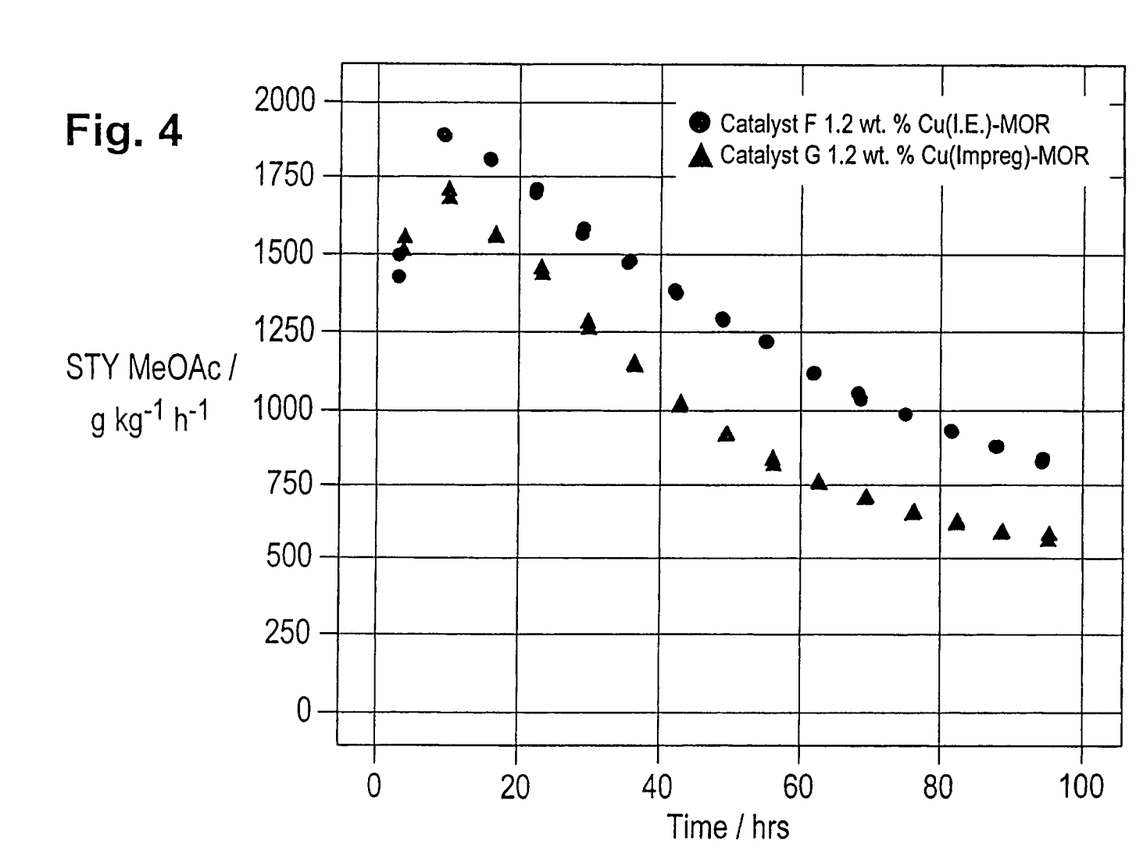
FIG. 4 depicts the STY to methyl acetate product in kg$^{-1}$ h$^{-1}$ versus time on stream for Cu-mordenite catalysts prepared by ion exchange and impregnation techniques and having the same copper loading.

FIG. 4 shows that Catalyst F prepared by ion-exchange has a higher activity than Catalyst G which is a catalyst having the same Cu loading, (1.2 weight % Cu) but prepared by impregnation.

Figure 5:
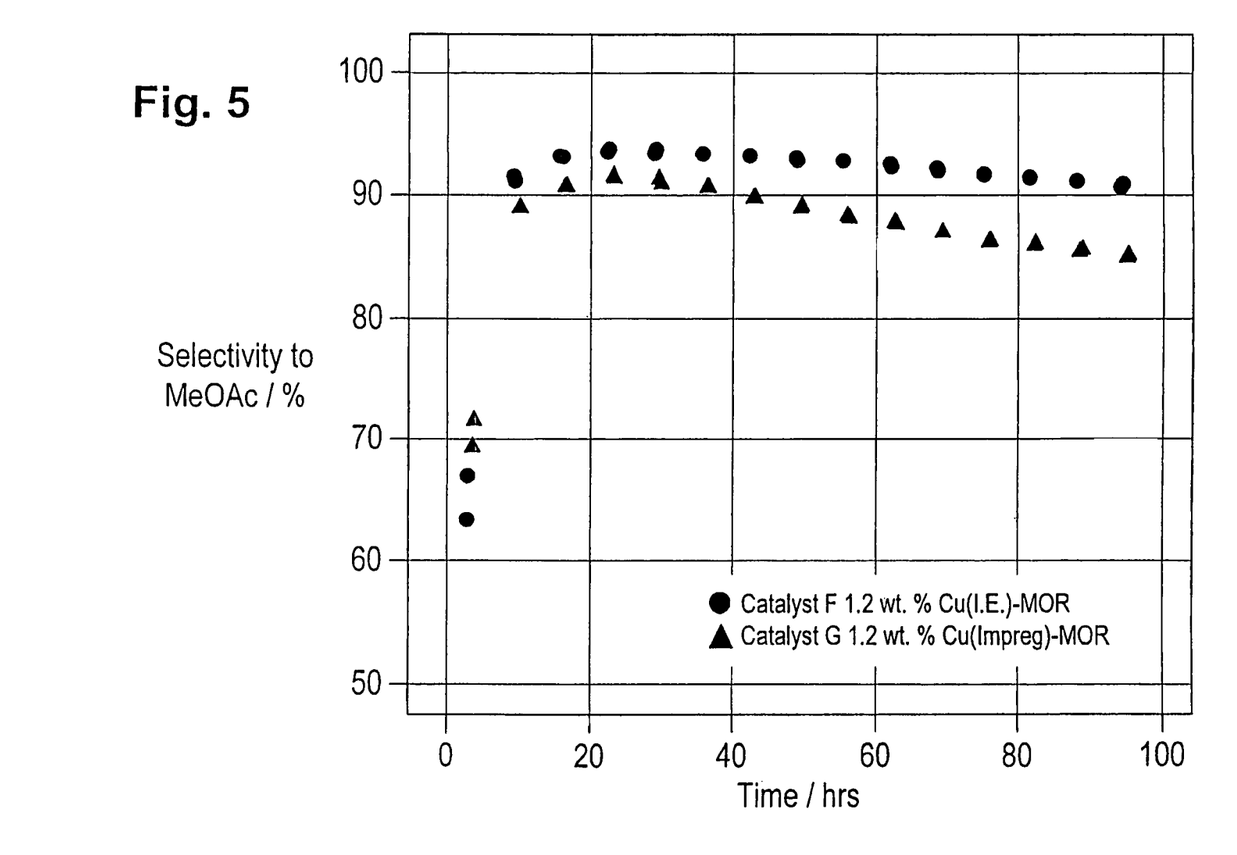
FIG. 5 depicts Selectivity to methyl acetate product versus time on stream for Cu-mordenite catalysts prepared by ion exchange and impregnation techniques and having the same copper loading.

FIG. 5 shows that Catalyst G prepared by ion-exchange has a higher selectivity to methyl acetate (based upon DME converted) than Catalyst G which is a catalyst having the same Cu loading, (1.2 weight % Cu) but prepared by impregnation.

The invention claimed is:

1. A process for the manufacture of methyl acetate comprising carbonylating a carbonylatable reactant selected from dimethyl ether and dimethyl carbonate containing less than 2.5 wt % water with carbon monoxide in the presence of a mordenite catalyst, wherein said mordenite has been ion-exchanged with at least one Group IB metal and the molar ratio of the Group IB metal to total aluminium present in the mordenite is in the range 5 to 50 mol %.

2. A process according to claim 1 wherein the mordenite is ion-exchanged with a Group IB metal selected from at least one of copper and silver.

3. A process according to claim 1 wherein the molar ratio of the Group IB metal to total aluminium is in the range 10 to 45 mol %.

4. A process according to claim 1 wherein the Group IB metal is copper and the molar ratio of copper to total aluminium is in the range 5 to 30 mol %.

5. A process according to claim 1 wherein the Group IB metal is silver and the molar ratio of silver to total aluminium is in the range 5 to 40 mol %.

6. A process according to claim 1 wherein the carbonylation is carried out in the presence of hydrogen.

7. A process according to claim 1 wherein methyl acetate is hydrolysed to form acetic acid.

8. A process according to claim 1 wherein the mordenite has been ion-exchanged with at least one Group IB metal by the steps of:
   (i) contacting the mordenite with an aqueous solution of at least one Group IB metal salt to produce a mordenite at or above its level of incipient wetness and excess metal salt solution;
   (ii) optionally heating the mordenite of step (i) at a temperature which maintains the level of incipient wetness and the excess metal salt solution remains as a solution;
   (iii) filtering the mordenite of step (i) or step (ii) to remove excess metal salt solution and to recover a solid Group IB metal loaded mordenite; and (iv) washing the solid Group IB metal loaded mordenite of step (iii) with a solvent to remove residual metal salt solution.

9. A process according to claim 8 wherein the aqueous solution of the Group IB metal salt is a solution of the Group IB metal salt in deionised water.

10. A process according to claim 8 wherein the aqueous solution of the Group IB metal salt is a solution of the Group IB metal salt in ammonium hydroxide solution in deionised water.

11. A process according to claim 8 wherein in step (ii) the mordenite is heated at a temperature in the range 60 to 90° C.

12. A process according to claim 8 wherein in step (iv) the solid Group IB metal loaded mordenite is washed with deionised water.

13. A process according to claim 8 wherein the ion-exchange further comprises the steps of:—
   (v) drying the washed mordenite of step (iv) to remove residual water;
   (vi) calcining the dried mordenite of step (v).

14. A process according to claim 13 wherein the drying is carried out at a temperature in the range 90 to 120° C.

15. A process according to claim 13 wherein the calcining is carried out at a temperature in the range 400 to 600° C.

* * * * *